(12) United States Patent
Ardelt

(10) Patent No.: US 6,239,257 B1
(45) Date of Patent: May 29, 2001

(54) FAMILY OF PROTEINS BELONGING TO THE PANCREATIC RIBONUCLEASE A SUPERFAMILY

(75) Inventor: Wojciech Ardelt, New City, NY (US)

(73) Assignee: Alfacell Corporation, Bloomfield, NJ (US)

( * ) Notice: Subject to any disclaimer, the term of this patent is extended or adjusted under 35 U.S.C. 154(b) by 0 days.

(21) Appl. No.: 09/223,118

(22) Filed: Dec. 30, 1998

(51) Int. Cl.[7] .................................................. C07K 14/475
(52) U.S. Cl. ........................ 530/350; 530/324; 530/395; 514/12; 514/21; 435/199
(58) Field of Search .................................... 530/350, 324, 530/395; 514/12, 21; 435/199

(56) References Cited

U.S. PATENT DOCUMENTS

| | | | |
|---|---|---|---|
| 4,882,421 | * 11/1989 | Shogen et al. | 530/350 |
| 5,559,212 | * 9/1996 | Ardelt | 530/350 |
| 5,728,805 | * 3/1998 | Ardelt | 530/350 |

OTHER PUBLICATIONS

Kamiya et al., *J. Biochem.*, vol. 108, pp. 139–143, 1990.*

Ardell et al., *The Journal of Biological Chemistry*, vol. 266, No. 1, pp. 245–251, Jan. 5, 1991.*

Mosimann et al., *Protein: Structure and Genetics*, vol. 14, pp. 392–400, 1992.*

* cited by examiner

*Primary Examiner*—Karen Cochrane Carlson
*Assistant Examiner*—Abdel A. Mohamed

(57) ABSTRACT

A protein family includes four proteins that are bioactive against human tumor cell lines. The proteins are derived from eggs of the *Rana pipiens* frog, and are members of the superfamily of pancreatic ribonucleases.

10 Claims, 8 Drawing Sheets

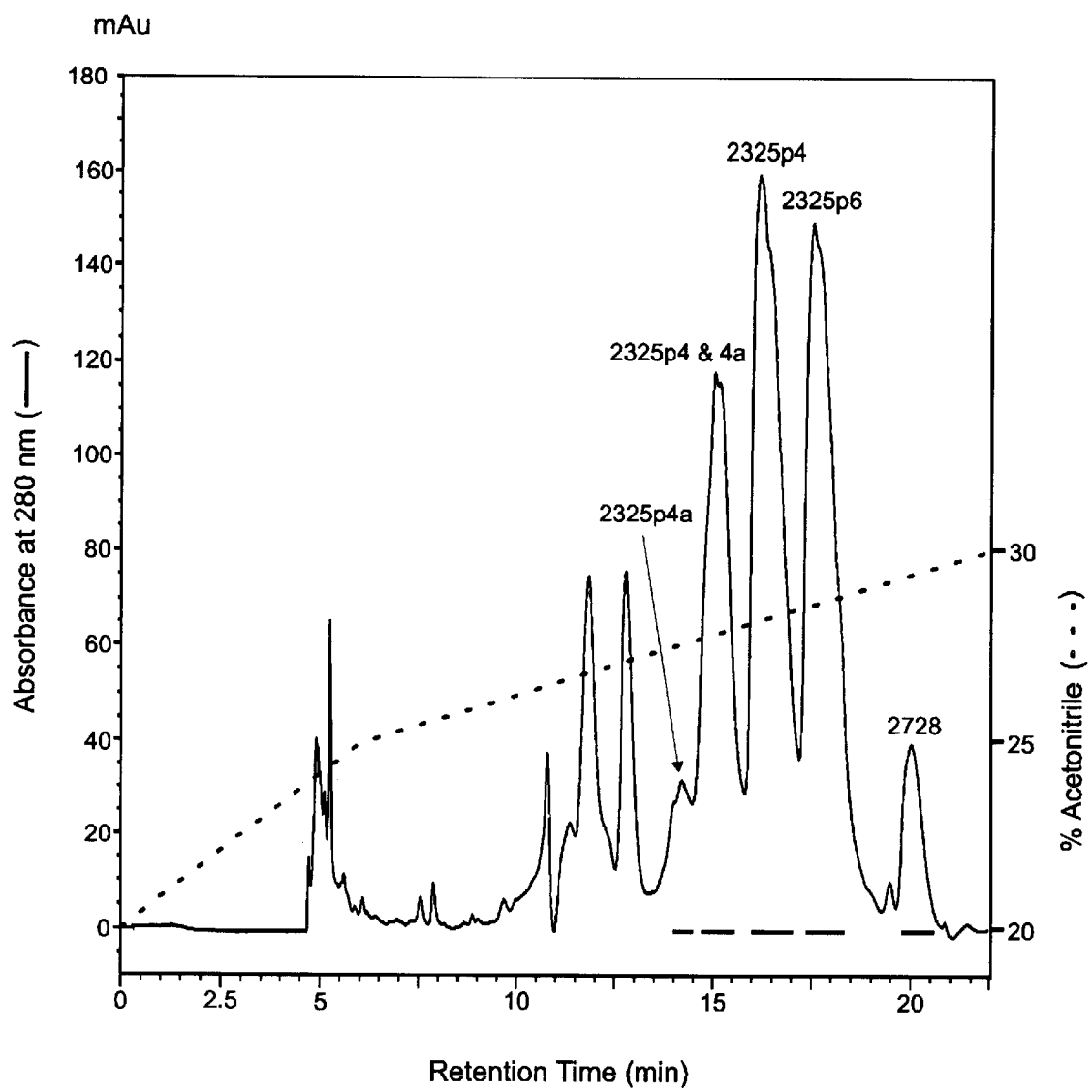
Figure 3  Reverse Phase Chromatography

Fig. 4

Amino Acid Sequence of (2325p4) Protein
SEQ ID NO:1

```
  1   2   3   4   5   6   7   8   9  10
Lys-Pro-Lys-Glu-Asp-Arg-Glu-Trp-Glu-Lys- 11                                  20
Phe-Lys-Thr-Lys-His-Ile-Thr-Ser-Gln-Ser- 21                                  30
Val-Ala-Asp-Phe-Asn-Cys-Asn-Arg-Thr-Met- 31                                  40
Asn-Asp-Pro-Ala-Tyr-Thr-Pro-Asp-Gly-Gln- 41                                  50
Cys-Lys-Pro-Ile-Asn-Thr-Phe-Ile-His-Ser- 51                                  60
Thr-Thr-Gly-Pro-Val-Lys-Glu-Ile-Cys-Arg- 61                                  70
Arg-Ala-Thr-Gly-Arg-Val-Asn-Lys-Ser-Ser- 71                                  80
Thr-Gln-Gln-Phe-Thr-Leu-Thr-Thr-Cys-Lys- 81                                  90
Asn-Pro-Ile-Arg-Cys-Lys-Tyr-Ser-Gln-Ser- 91                                 100
Asn-Thr-Thr-Asn-Phe-Ile-Cys-Ile-Thr-Cys- 101                                 110
Arg-Asp-Asn-Tyr-Pro-Val-His-Phe-Val-Lys- 111         114
Thr-Gly-Lys-Cys
```

Fig.5

Amino Acid Sequence of (2325p4a) Protein
SEQ ID NO:2

```
  1   2   3   4   5   6   7   8   9  10
Lys-Pro-Lys-Glu-Asp-Arg-Glu-Trp-Glu-Lys- 11                                  20
Phe-Lys-Thr-Lys-His-Ile-Thr-Ser-Gln-Ser- 21                                  30
Val-Ala-Asp-Phe-Asn-Cys-Asn-Arg-Thr-Met- 31                                  40
Asn-Asp-Pro-Ala-Tyr-Thr-Pro-Asp-Gly-Gln- 41                                  50
Cys-Lys-Pro-Val-Asn-Thr-Phe-Ile-His-Ser- 51                                  60
Thr-Thr-Gly-Pro-Val-Lys-Glu-Ile-Cys-Arg- 61                                  70
Arg-Ala-Thr-Gly-Arg-Val-Asn-Lys-Ser-Ser- 71                                  80
Thr-Gln-Gln-Phe-Thr-Leu-Thr-Thr-Cys-Lys- 81                                  90
Asn-Pro-Ile-Arg-Cys-Lys-Tyr-Ser-Gln-Ser- 91                                 100
Asn-Thr-Thr-Asn-Phe-Ile-Cys-Ile-Thr-Cys- 101                                 110
Arg-Asp-Asn-Tyr-Pro-Val-His-Phe-Val-Lys- 111         114
Thr-Gly-Lys-Cys
```

Fig.6

Amino Acid Sequence of (2325p6) Protein
SEQ ID NO: 3

```
  1   2   3   4   5   6   7   8   9  10
Lys-Pro-Lys-Glu-Asp-Lys-Glu-Trp-Glu-Lys- 11                                  20
Phe-Lys-Val-Lys-His-Ile-Thr-Ser-Gln-Ser- 21                                  30
Val-Ala-Asp-Phe-Asn-Cys-Thr-Ser-Thr-Met- 31                                  40
Asn-Asn-Pro-Asp-Phe-Thr-Pro-Asp-Gly-Gln- 41                                  50
Cys-Lys-Pro-Ile-Asn-Thr-Phe-Ile-His-Ser- 51                                  60
Asn-Thr-Gly-Pro-Val-Lys-Glu-Ile-Cys-Arg- 61                                  70
Arg-Ala-Ser-Gly-Arg-Val-Asn-Lys-Ser-Ser- 71                                  80
Thr-Gln-Gln-Phe-Pro-Leu-Thr-Thr-Cys-Lys- 81                                  90
Asn-Pro-Lys-Arg-Cys-Lys-Tyr-Ser-Gln-Ser- 91                                 100
Asn-Glu-Thr-Asn-Tyr-Ile-Cys-Ile-Thr-Cys- 101                                 110
Arg-Asp-Asn-Tyr-Pro-Val-His-Phe-Val-Lys- 111         114
Ile-Gly-Lys-Cys
```

Fig. 7

Amino-Acid Sequence of (2728) Protein
SEQ ID NO:4

```
  1   2   3   4   5   6   7   8   9   10
Lys-Pro-Lys-Glu-Asp-Lys-Glu-Trp-Val-Lys- 11                                    20
Phe-Lys-Ala-Lys-His-Ile-Thr-Ser-Gln-Ser- 21                                    30
Val-Ala-Asp-Phe-Asn-Cys-Asn-Lys-Thr-Met- 31                                    40
Asn-Asp-Pro-Asp-Phe-Thr-Pro-Asp-Gly-Gln- 41                                    50
Cys-Lys-Pro-Val-Asn-Thr-Phe-Ile-His-Ser- 51                                    60
Asn-Thr-Gly-Pro-Val-Lys-Asp-Ile-Cys-Arg- 61                                    70
Arg-Ala-Ser-Gly-Arg-Val-Asn-Lys-Ser-Ser- 71                                    80
Thr-Gln-Gln-Phe-Pro-Leu-Thr-Thr-Cys-Asn- 81                                    90
Lys-Pro-Ile-Arg-Cys-Lys-Tyr-Ser-Gln-Ser- 91                                   100
Asn-Thr-Thr-Asn-Phe-Ile-Cys-Ile-Thr-Cys 101                                   110
Arg-Asp-Asn-Tyr-Pro-Val-His-Phe-Val-Lys- 111         114
Ile-Gly-Lys-Cys
```

Figure 8

HOMOLOGY OF PROTEINS: IDENTICAL AMINO ACID RESIDUES IN BOXES

```
         1                  10                   20                   30                   40                   50
2325P4   K P K E D R E W E K F K T K H I T S Q S V A D F N C N R T M N D P A Y T P D G Q C K P I N T F I H S T T G P V K E I C R
2325P4a  K P K E D R E W E K F K T K H I T S Q S V A D F N C N R T M N D P A Y T P D G Q C K P I N T F I H S T T G P V K E I C R
2325P6   K P K E D K E W E K F K V K H I T S Q S V A D F N C N R T M N N P D F T P D G Q C K P I N T F I H S N T G P V K E I C R
2728     K P K E D K E W V K F K A K H I T S Q S V A D F N C N K T M N D P D F T P D G Q C K P V N T F I H S N T G P V K D I C R 61                 70                   80                   90                  100                  110       114
2325P4   R A T G R V N K S S T Q Q F T L T T C K N P I R C K Y S Q S N T T N F I C I T C R D N Y P V H F V K T G K C
2325P4a  R A T G R V N K S S T Q Q F T L T T C K N P I R C K Y S Q S N T T N F I C I T C R D N Y P V H F V K T G K C
2325P6   R A S G R V N K S S T Q Q F P L T T C K N P K R C K Y S Q S N E T N Y I C I T C R D N Y P V H F V K I G K C
2728     R A S G R V N K S S T Q Q F P L T T C N K P I R C K Y S Q S N T T N F I C I T C R D N Y P V H F V K I G K C
``` ent shown in FIG. 1, *Rana pipiens* eggs are accumulated

FAMILY OF PROTEINS BELONGING TO THE PANCREATIC RIBONUCLEASE A SUPERFAMILY

BACKGROUND OF THE INVENTION

The invention relates to pharmaceuticals, and more particularly relates to pharmaceuticals for use in treating tumors in humans.

One object of the invention is to provide a family of pharmaceuticals for use in treating tumors in humans.

Another object is, in general, to improve upon known therapies for treatment of tumors in humans.

In accordance with the invention, there is a provided a family of highly-homologous and closely related proteins. The family is exemplified by four purified proteins, each having a) an amino acid sequence that is 114 amino acids long, b) an isoelectric point of approximately 10, and c) a molecular weight of approximately 13,000. Advantageously although not necessarily, the proteins are derived from frog eggs and preferably from the eggs of the *Rana pipiens* frog.

The above-referenced four purified proteins are glycoproteins, i.e. each contains glycans (carbohydrates) that are linked to the protein by covalent bonds. However, the glycan moieties are not necessary for the bioactivity of the proteins against human tumor cell lines.

U.S. Pat. Nos. 5,559,212 and 5,728,805 disclose two protein peaks coming off a cationic-exchange chromatography column. U.S. Pat. No. 5,559,212 describes the amino acid sequence and composition of the protein in the first (larger) peak, and the disclosure of U.S. Pat. No. 5,728,805 extends this description by describing the amino acid sequence and composition of the protein in the second (smaller) peak. A third protein peak also comes off the ion-exchange column, and this (still smaller) peak has now been shown to contain four proteins that are sufficiently similar to justify their designation as a family. Because the third protein peak is eluted after the first and second peaks, the proteins in that peak are more basic.

Tests have shown that each of the four proteins possesses bioactivity against two human carcinoma cell lines.

BRIEF DESCRIPTION OF THE DRAWINGS

The invention will be better understood with reference to the following illustrative and non-limiting drawings, in which:

FIG. 3 shows the results of the reversed-phase high performance liquid chromatography step, and illustrates the fractions that contained the four proteins herein described;

FIG. 4 shows the amino acid sequence of the first of the four proteins herein described, namely the protein having SEQ ID NO: 1 as its amino acid sequence;

FIG. 5 shows the amino acid sequence of the second of the four proteins herein described, namely the protein having SEQ ID NO: 2 as its amino acid sequence;

FIG. 6 shows the amino acid sequence of the third of the four proteins herein described, namely the protein having SEQ ID NO: 3 as its amino acid sequence;

FIG. 7 shows the amino acid sequence of the fourth of the four proteins herein described, namely the protein having SEQ ID NO: 4 as its amino acid sequence; and FIG. 8 illustrates the homology between the four proteins herein described.

DETAILED DESCRIPTION OF PREFERRED EMBODIMENTS

Figure 1:
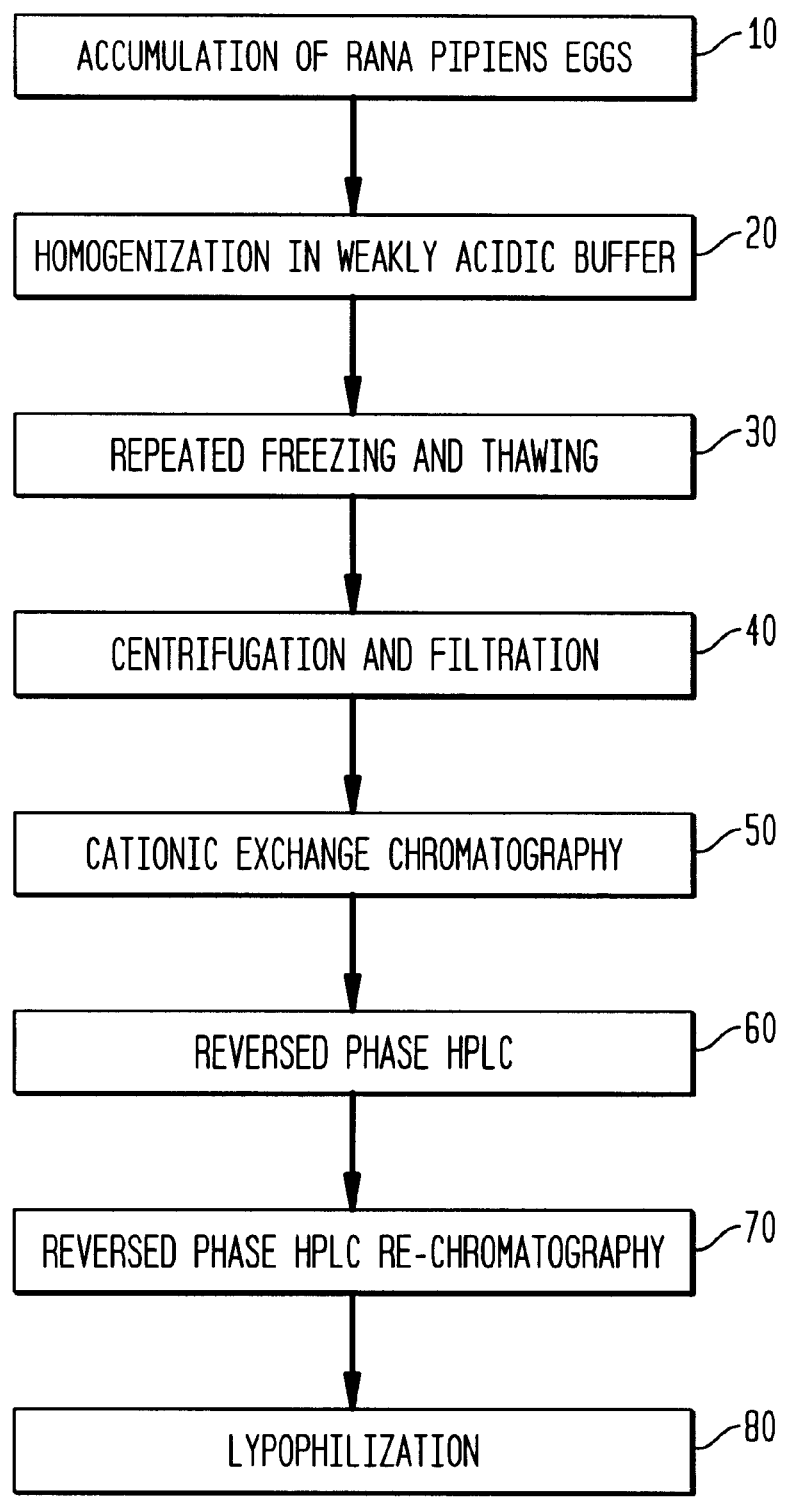
FIG. 1 is a flow chart showing how the four proteins are produced and purified.

Initially, and in accordance with the preferred embodiment shown in FIG. 1, *Rana pipiens* eggs are accumulated (step 10), homogenized in a weakly acidic buffer (step 20), repeatedly frozen and thawed (step 30), centrifuged and filtered (step, 40). The accumulation, homogenization, freezing, and thawing steps are described at column 3, lines 1 to 54. 103 g of thawed *Rana pipiens* eggs were combined at room temperature with 206 mL of 0.15 M sodium acetate buffer, pH 5.0. This mixture was then homogenized in a Waring Blender for 3 minutes at high speed. The resulting homogenate was repeatedly (four times) frozen to −20 °C. (±10° C.) and thawed. The thawed homogenate was then centrifuged at 10,000×g for 25 minutes, and the supernatent was then filtered through a filter paper (Whatman, No. 541) yielding 248 mL of clear extract, which had 1455 absorbance units of UV light having a wavelength of 280 nm.

The 248 mL of clear extract is then (step 50) subjected to cationic exchange chromatography, essentially as described in U.S. Pat. No. 5,728,805 at column 6, lines 50–64. Specifically, the clear extract was loaded on a chromatographic column packed with SP Sepharose FF (Pharmacia) resin to form a bed that is 2.5 cm in diameter and 6.7 cm long. The packed column was equilibrated in 0.15 M sodium acetate buffer, pH 5.0 and the chromatography was carried out at room temperature with the extract being loaded onto the column at a flow rate of 3 mL/min. The packed column was first washed with the equilibrating buffer and then (beginning at fraction 78) developed with a continuous (from 0 M to 0.46 M) sodium chloride gradient made in the equilibrating buffer. Eluate fractions of 4.8 mL were automatically collected while continuously monitoring the absorption of 280 nm UV light. The total volume of the gradient was 800 mL.

The eluate collected in the first 77 fractions is inactive, and was discarded. The protein in the first (largest) protein peak eluted in fractions 120 to 133 is described in U.S. Pat. No. 5,559,212, and the protein in the second (smaller) protein peak eluted in fractions 158 to 166 is described in U.S. Pat. No. 5,728,805. The proteins herein described are contained in the third (smallest) protein peak eluted in fractions 194 to 210. The total quantity of "third peak" material eluted in fractions 194 to 210 was 16.6 absorbance units of 280 nm UV light (about 1.14% of the material loaded onto the column), corresponding to about 25 mg.

The eluted "third peak" material from fractions 194 to 210 was then subjected to reversed-phase high performance liquid chromatography (step 60 in FIG. 1). The chromatography was conducted on a Zorbax SB300 C18 column having a diameter of 9.4 mm and a length of 250 mm. The column was attached to a Hewlett-Packard Series 1090 Liquid Chromatograph.

The eluted "third peak" material was loaded onto the column in 5 mg aliquots, at a temperature of 35° C. The column was equilibrated in 0.1% (v/v) trifluoroacetic acid (Buffer A) and developed with a gradient of acetonitrile/ 0.1% trifluoroacetic acid (Buffer B). The following elution method was employed after the loading: from the beginning of the chromatography to six minutes afterward, the slope of the gradient was increased from 20% Buffer B to 24.4% Buffer B. Thereafter, from minute 6 until minute 24, the slope of the gradient was increased from 24.4% Buffer B to 30% Buffer B. Protein peaks were collected manually. Equivalent peaks from 5 different runs (i.e. 5 aliquots of 5 mg each) were combined.

An exemplary chromatographic pattern is presented in FIG. 3. The material eluted between 4.5 and 13.5 min of the run had no cytotoxic activity and was discarded. The proteins contained in the five major peaks eluted between 13.5 and 21 min proved to be bioactive as discussed below. These proteins were collected as indicated by the solid bars in FIG. 3 and were further purified.

The major peak (denoted 2325p4 in FIG. 3) eluted at minutes 16 to 17 contained the protein (SEQ ID NO:1) most represented in the source. The small peak (denoted 2325p4a in FIG. 3) eluted at about 14 min contained a highly similar protein (SEQ ID NO:2) differing therefrom by only one amino acid residue. The peak eluted between minutes 14.5 and 15.5 contained a mixture of these two proteins. The remaining two peaks (denoted, respectively, 2325p6 and 2728 in FIG. 3) eluting from the column at 17 to 18.5 minutes and 19.5 to 20.5 minutes, respectively, contained two other proteins (SEQ ID NO:3 and SEQ ID NO:4, respectively).

All the isolated proteins were re-chromatographed (step 70 in FIG. 1) on the same column under identical conditions (patterns not shown) and lyophilized (step 80). The final yield of the individual proteins (from five runs) was as follows: SEQ ID NO:1, 5.7 mg (from the peak eluted from minute 14 to minute 16); SEQ ID NO:2, 1 mg (from the peak eluted at about 14 minutes); SEQ ID NO:3, 6.5 mg; SEQ ID NO:4, 1.3 mg. The peak that contained a mixture of the SEQ ID NO:1 and the SEQ ID NO:2 proteins yielded 4.6 mg.

The proteins isolated by the procedure described above were chemically and biologically characterized using amino acid sequencing and cytotoxicity studies. At the scale described above, the purification process was repeated several times to generate sufficient material.

FIGS. 4–7 show the amino acid sequences of the four proteins that were isolated and purified as discussed above. As can be seen in FIG. 8, the four proteins are so similar that they can be said to define a family. 95 residues (i.e. 83.3% of all 114 residues) are identical in all four proteins. The remaining 19 positions, namely positions 6, 9, 13, 27, 28, 32, 34, 35, 44, 51, 57, 63, 75, 80, 81, 83, 92, 95, and 111, are polymorphic. Only one residue is different between 2325p4 and 2325p4a (SEQ ID NO:1 and SEQ ID NO:2), so those proteins are 99.1% homologous. Other side-to-side comparisons revealed the following percentages of homology:

2325p6 vs 2728: 89.5%

2325p4 vs 2325p6: 87.7%

2325p4a vs 2728: 88.6%

2325p4 vs 2728: 87.7%

2325p4a vs 2325p6: 86.8%.

Version BLASTP of the BLAST (Basic Local Alignment Search Tool) program was used to check the relationships between the four proteins and 300,806 known protein sequences at the National Center for Biotechnology Information. This search revealed that each of the four proteins, and therefore the family in which they are included, belongs to the pancreatic ribonuclease A superfamily.

Tables 1–5 below show the amino acid compositions of the referenced four proteins; Tables 1–4 show mole percentages after hydrolysis, while Table 5 shows the number of amino acid residues per molecule.

Compositional analysis of these four proteins was carried out using a pre-column derivatization method with 6-Aminoqinolyl-N-Hydroxysuccinimidyl Carbamate. Derivatized amino acids were identified and quantified by a reversed phase chromatography on a C8 column (Zorbax, Eclipse XDB 2.1×150 mm) using a Hewlett-Packard Series 1090 Liquid Chromatograph. Prior to manual hydrolysis in 6.0 M hydrochloric acid (21 h at 105–110° C. in evacuated tubes) the protein samples were denatured, their disulfide bonds were reduced and the newly formed sulfhydryl groups were alkylated with 4-vinyl pyridine. The purpose of this sample preparation was to protect cysteine, which is largely destroyed during acid hydrolysis. The apparent cysteine content is usually somewhat lowered even in alkylated samples, because alkylation does not proceed to completion. Tryptophan, another amino acid destroyed by acid hydrolysis, was not determined. The values for serine, threonine, and methionine, which all undergo partial destruction during acid hydrolysis, were uncorrected. Also uncorrected were values for isoleucine (peptide bonds formed by this amino acid are more resistant to hydrolysis than are ordinary peptide bonds).

TABLE 1

Amino Acid Composition of (2325p4) Protein
SEQ ID NO: 1

| Amino Acid Residue | Mole % (21 hour hydrolysis) | |
|---|---|---|
| | Found | From Sequence |
| Alanine | 2.68 | 2.63 |
| Arginine | 6.00 | 6.14 |
| Aspartic acid/Asparagine | 13.35 | 12.28 |
| Cysteine[1] | 6.44 | 7.02 |
| Glutamic acid/Glutamine | 8.48 | 7.89 |
| Glycine | 3.80 | 3.51 |
| Histidine | 2.41 | 2.63 |
| Isoleucine[2] | 6.05 | 6.14 |
| Leucine | 0.93 | 0.88 |
| Lysine | 10.43 | 10.53 |
| Methionine[3] | 0.64 | 0.88 |
| Phenylalanine | 5.39 | 5.26 |
| Proline | 6.93 | 6.14 |
| Serine[3] | 6.05 | 6.14 |
| Threonine[3] | 13.38 | 14.04 |
| Tryptophan | ND | 0.88 |
| Tyrosine | 2.61 | 2.63 |
| Valine | 4.42 | 4.39 |
| Total | 99.99 | 100.00 |

ND, not determined;
[1] as a pyridylethyl derivative;
[2] ucorrected for incomplete hydrolysis;
[3] uncorrected for destruction.

TABLE 2

Amino Acid Composition of (2325p4a) Protein
SEQ ID NO: 2

| Amino Acid Residue | Mole % (21 hour hydrolysis) | |
|---|---|---|
| | Found | From Sequence |
| Alanine | 2.86 | 2.63 |
| Arginine | 6.31 | 6.14 |
| Aspartic acid/Asparagine | 12.71 | 12.28 |
| Cysteine[1] | 6.44 | 7.02 |
| Glutamic acid/Glutamine | 8.26 | 7.89 |
| Glycine | 4.32 | 3.51 |
| Histidine | 2.40 | 2.63 |
| Isoleucine[2] | 5.14 | 5.26 |

TABLE 2-continued

Amino Acid Composition of (2325p4a) Protein SEQ ID NO: 2

| Amino Acid Residue | Mole % (21 hour hydrolysis) | |
|---|---|---|
| | Found | From Sequence |
| Leucine | 1.08 | 0.88 |
| Lysine | 9.90 | 10.53 |
| Methionine[3] | 0.72 | 0.88 |
| Phenylalanine | 5.37 | 5.26 |
| Proline | 6.57 | 6.14 |
| Serine[3] | 6.07 | 6.14 |
| Threonine[3] | 13.96 | 14.04 |
| Tryptophan | ND | 0.88 |
| Tyrosine | 2.68 | 2.63 |
| Valine | 5.21 | 5.26 |
| Total | 100.00 | 99.99 |

ND, not determined;
[1] as a pyridylethyl derivative;
[2] ucorrected for incomplete hydrolysis;
[3] uncorrected for destruction.

TABLE 3

Amino Acid Composition of (2325p6) Protein SEQ ID NO: 3

| Amino Acid Residue | Mole % (21 hour hydrolysis) | |
|---|---|---|
| | Found | From Sequence |
| Alanine | 1.97 | 1.75 |
| Arginine | 4.50 | 4.39 |
| Aspartic acid/Asparagine | 14.37 | 13.16 |
| Cysteine[1] | 6.23 | 7.02 |
| Glutamic acid/Glutamine | 9.37 | 8.77 |
| Glycine | 3.77 | 3.51 |
| Histidine | 2.32 | 2.63 |
| Isoleucine[2] | 6.07 | 6.14 |
| Leucine | 0.95 | 0.88 |
| Lysine | 11.76 | 12.28 |
| Methionine[3] | 0.74 | 0.88 |
| Phenylalanine | 5.38 | 5.26 |
| Proline | 7.56 | 7.02 |
| Serine[3] | 7.44 | 7.89 |
| Threonine[3] | 9.70 | 9.65 |
| Tryptophan | ND | 0.88 |
| Tyrosine | 2.68 | 2.63 |
| Valine | 5.20 | 5.26 |
| Total | 100.01 | 100.00 |

ND, not determined;
[1] as a pyridylethyl derivative;
[2] ucorrected for incomplete hydrolysis;
[3] uncorrected for destruction.

TABLE 4

Amino Acid Composition of (2728) Protein SEQ ID NO: 4

| Amino Acid Residue | Mole % (21 hour hydrolysis) | |
|---|---|---|
| | Found | From Sequence |
| Alanine | 2.74 | 2.63 |
| Arginine | 4.52 | 4.39 |
| Aspartic acid/Asparagine | 15.36 | 14.91 |
| Cysteine[1] | 6.77 | 7.02 |
| Glutamic acid/Glutamine | 6.50 | 6.14 |
| Glycine | 3.76 | 3.51 |
| Histidine | 2.47 | 2.63 |
| Isoleucine[2] | 6.19 | 6.14 |
| Leucine | 0.89 | 0.88 |
| Lysine | 11.96 | 12.28 |
| Methionine[3] | 0.85 | 0.88 |
| Phenylalanine | 6.26 | 6.14 |
| Proline | 7.51 | 7.02 |
| Serine[3] | 6.66 | 7.02 |
| Threonine[3] | 9.50 | 9.65 |
| Tryptophan | ND | 0.88 |
| Tyrosine | 1.85 | 1.75 |
| Valine | 6.22 | 6.14 |
| Total | 100.01 | 100.02 |

ND, not determined;
[1] as a pyridylethyl derivative;
[2] ucorrected for incomplete hydrolysis;
[3] uncorrected for destruction.

TABLE 5

Amino Acid Composition of Four Proteins (as calculated from their amino acid sequences)

| Amino Acid | Number of Residues Per Molecule | | | |
|---|---|---|---|---|
| | (2325p4) | (2325p4a) | (2325p6) | (2728) |
| Alanine | 3 | 3 | 2 | 3 |
| Arginine | 7 | 7 | 5 | 5 |
| Asparagine | 9 | 9 | 10 | 10 |
| Aspartic acid | 5 | 5 | 5 | 7 |
| Cysteine | 8 | 8 | 8 | 8 |
| Glutamine | 5 | 5 | 5 | 5 |
| Glutamic acid | 4 | 4 | 5 | 2 |
| Glycine | 4 | 4 | 4 | 4 |
| Histidine | 3 | 3 | 3 | 3 |
| Isoleucine | 7 | 6 | 7 | 7 |
| Leucine | 1 | 1 | 1 | 1 |
| Lysine | 12 | 12 | 14 | 14 |
| Methionine | 1 | 1 | 1 | 1 |
| Phenylalanine | 6 | 6 | 6 | 7 |
| Proline | 7 | 7 | 8 | 8 |
| Serine | 7 | 7 | 9 | 8 |
| Threonine | 16 | 16 | 11 | 11 |
| Tryptophan | 1 | 1 | 1 | 1 |
| Tyrosine | 3 | 3 | 3 | 2 |
| Valine | 5 | 6 | 6 | 7 |
| Total | 114 | 114 | 114 | 114 |

As stated above, these proteins are glycoproteins, which are heterogeneous on polyacrylamide gel electrophoresis. For this reason, polyacrylamide gel electrophoresis can only produce a range of their apparent molecular weights.

An apparent molecular weight range of 13,000 to 20,000 was estimated by SDS-PAGE (polyacrylamide gel electrophoresis in the presence of sodium dodecyl sulfate) using a 10%–20% gradient gel and a Tricine buffer system. This range represents the molecular weight of entire molecules of each protein, i.e. represents the molecular weight not only of the protein itself but of the glycans that are attached to it.

Molecular weight values of the protein moieties of each protein were calculated from its complete amino acid sequences (FIGS. 4–7) assuming that all eight cysteine residues were paired to form four disulfide bridges.

The isolectric point of each protein was also calculated from each sequence using the same assumption of cysteine pairing. Molecular weights and isoelectric points were calculated using the Protein Tools Version 5.04 computer program (1996), Window Chem Software, Inc. The values are presented in Table 6.

Figure 2:
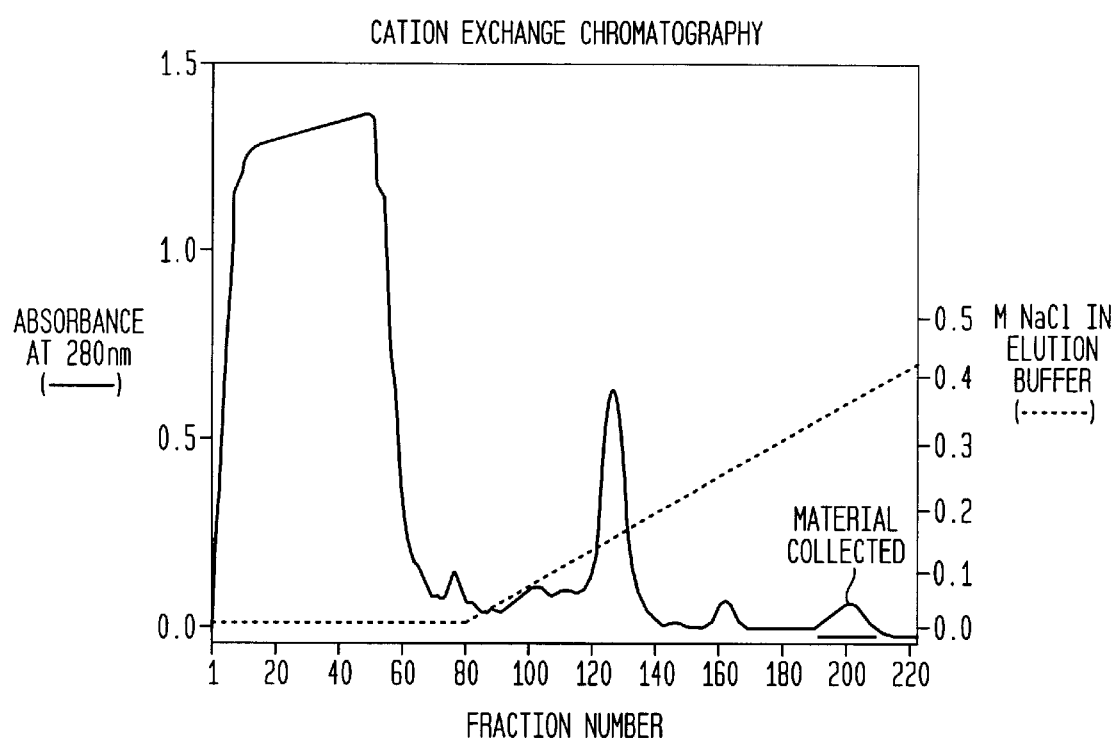
FIG. 2 shows the results of the cationic exchange chromatography step and illustrates the fractions from which the four proteins are isolated and purified.

As can be seen from Table 6, the molecular weight of each of the proteins is approximately 13,000. The isolectric point of each of these proteins is approximately 10, which agrees well with their behavior on a cationic exchange column (FIG. 2).

TABLE 6

Physical Parameters of Proteins
(as calculated from their amino acid sequences)

| Protein | Molecular Weight | Isoelectric Point |
|---|---|---|
| 2325p4 | 13077 | 10.16 |
| 2325p4a | 13063 | 10.16 |
| 2325p6 | 13058 | 9.95 |
| 2728 | 12968 | 10.10 |

As stated above, all four proteins are glycoproteins, i.e. each contains glycans (carbohydrates) that are linked to the protein by covalent bonds. These glycan moieties are not essential for bioactivity. Glycan content apparently varies from one protein to another as well as from one molecule of a protein to another molecule of the same protein. As estimated using the Glycoprotein Carbohydrate Estimation Kit (Pierce), each protein contains at least several percent glycans.

Each protein is glycosylated at more than one site. Glycan moieties were found attached to asparagine residues (N-glycosylation). To date, two glycosylation sites have been determined for each protein. They are Asn 27 and 91 in proteins 2325p4, 2325p4a, and 2728 (SEQ ID NO:1, SEQ ID NO:2, and SEQ ID NO:4 respectively). In protein 2325p6 (SEQ ID NO:3) glycosylated residues are Asn 25 and 91. It appears that the size and the chemical nature of the glycan moieties vary from one molecule of a particular protein to another.

The herein-described proteins were tested for bioactivity against two human carcinoma cell lines, namely human submaxillary gland carcinoma (A-253) and human bladder carcinoma (T-24). The results of these tests are shown in Tables 7 and 8. Ranpirnase (known by its trademark ONCONASE and disclosed in U.S. Pat. No. 5,559,212) and bovine ribonuclease A served, respectively, as positive and negative controls.

As can be seen in Tables 7 and 8, each protein strongly inhibited growth of each cell line; A-253 human submaxillary gland carcinoma cells turned out to be more responsive. Antiproliferative/cytotoxic activities of the proteins were comparable to that of Ranpirnase. Ribonuclease A had only a negligible effect even when used at substantially higher concentrations.

TABLE 7

Effect Of Proteins and Related Ribonucleases on Growth Of Human Submaxillary Gland Carcinoma (A-253) Cells

| PROTEIN | GROWTH INHIBITION | |
|---|---|---|
| | MEAN % | (SD) |
| 2325p4 | 97.1 | (0.13) |
| 2325p4a | 88.0 | (0.56) |
| 2325p6 | 98.2 | (0.74) |
| 2728 | 90.6 | (4.99) |
| Ranpirnase | 85.5 | (4.91) |
| Ribonuclease A | 8.0 | (6.61) |

Mean values of four experiments
Protein concentrations were 1.0 µg/mL except Ribonuclease A (which was 10 µg/mL).
SD = standard deviation.

TABLE 8

Effect Of Proteins and Ranpirnase
On Growth of Human Bladder Carcinoma (T-24) Cells

| PROTEIN | GROWTH INHIBITION | |
|---|---|---|
| | MEAN % | (SD) |
| 2325p4 | 63.9 | (11.9) |
| 2325p4a | 68.4 | (10.2) |
| 2325P6 | 71.9 | (8.0) |
| 2728 | 61.5 | (8.7) |
| Ranpirnase | 68.5 | (9.5) |

Mean values of four experiments
Protein concentrations were 2.0 µg/mL.
SD = standard deviation.

SEQUENCE LISTING

<160> NUMBER OF SEQ ID NOS: 4

<210> SEQ ID NO 1
<211> LENGTH: 114
<212> TYPE: PRT
<213> ORGANISM: Rana pipiens

<400> SEQUENCE: 1

Lys Pro Lys Glu Asp Arg Glu Trp Glu Lys Phe Lys Thr Lys His Ile
 1               5                   10                  15

Thr Ser Gln Ser Val Ala Asp Phe Asn Cys Asn Arg Thr Met Asn Asp

-continued

```
                    20                  25                  30
Pro Ala Tyr Thr Pro Asp Gly Gln Cys Lys Pro Ile Asn Thr Phe Ile
                35                  40                  45
His Ser Thr Thr Gly Pro Val Lys Glu Ile Cys Arg Arg Ala Thr Gly
         50                  55                  60
Arg Val Asn Lys Ser Ser Thr Gln Gln Phe Thr Leu Thr Thr Cys Lys
 65                  70                  75                  80
Asn Pro Ile Arg Cys Lys Tyr Ser Gln Ser Asn Thr Thr Asn Phe Ile
                 85                  90                  95
Cys Ile Thr Cys Arg Asp Asn Tyr Pro Val His Phe Val Lys Thr Gly
                100                 105                 110
Lys Cys

<210> SEQ ID NO 2
<211> LENGTH: 114
<212> TYPE: PRT
<213> ORGANISM: Rana pipiens

<400> SEQUENCE: 2

Lys Pro Lys Glu Asp Arg Glu Trp Glu Lys Phe Lys Thr Lys His Ile
 1               5                  10                  15
Thr Ser Gln Ser Val Ala Asp Phe Asn Cys Asn Arg Thr Met Asn Asp
                20                  25                  30
Pro Ala Tyr Thr Pro Asp Gly Gln Cys Lys Pro Val Asn Thr Phe Ile
                35                  40                  45
His Ser Thr Thr Gly Pro Val Lys Glu Ile Cys Arg Arg Ala Thr Gly
         50                  55                  60
Arg Val Asn Lys Ser Ser Thr Gln Gln Phe Thr Leu Thr Thr Cys Lys
 65                  70                  75                  80
Asn Pro Ile Arg Cys Lys Tyr Ser Gln Ser Asn Thr Thr Asn Phe Ile
                 85                  90                  95
Cys Ile Thr Cys Arg Asp Asn Tyr Pro Val His Phe Val Lys Thr Gly
                100                 105                 110
Lys Cys

<210> SEQ ID NO 3
<211> LENGTH: 114
<212> TYPE: PRT
<213> ORGANISM: Rana pipiens

<400> SEQUENCE: 3

Lys Pro Lys Glu Asp Lys Glu Trp Glu Lys Phe Lys Val Lys His Ile
 1               5                  10                  15
Thr Ser Gln Ser Val Ala Asp Phe Asn Cys Thr Ser Thr Met Asn Asn
                20                  25                  30
Pro Asp Phe Thr Pro Asp Gly Gln Cys Lys Pro Ile Asn Thr Phe Ile
                35                  40                  45
His Ser Asn Thr Gly Pro Val Lys Glu Ile Cys Arg Arg Ala Ser Gly
         50                  55                  60
Arg Val Asn Lys Ser Ser Thr Gln Gln Phe Pro Leu Thr Thr Cys Lys
 65                  70                  75                  80
Asn Pro Lys Arg Cys Lys Tyr Ser Gln Ser Asn Glu Thr Asn Tyr Ile
                 85                  90                  95
Cys Ile Thr Cys Arg Asp Asn Tyr Pro Val His Phe Val Lys Ile Gly
                100                 105                 110
```

-continued

```
Lys Cys

<210> SEQ ID NO 4
<211> LENGTH: 114
<212> TYPE: PRT
<213> ORGANISM: Rana pipiens

<400> SEQUENCE: 4

Lys Pro Lys Glu Asp Lys Glu Trp Val Lys Phe Lys Ala Lys His Ile
 1               5                  10                  15

Thr Ser Gln Ser Val Ala Asp Phe Asn Cys Asn Lys Thr Met Asn Asp
            20                  25                  30

Pro Asp Phe Thr Pro Asp Gly Gln Cys Lys Pro Val Asn Thr Phe Ile
         35                  40                  45

His Ser Asn Thr Gly Pro Val Lys Asp Ile Cys Arg Arg Ala Ser Gly
     50                  55                  60

Arg Val Asn Lys Ser Ser Thr Gln Gln Phe Pro Leu Thr Thr Cys Asn
 65                  70                  75                  80

Lys Pro Ile Arg Cys Lys Tyr Ser Gln Ser Asn Thr Thr Asn Phe Ile
                 85                  90                  95

Cys Ile Thr Cys Arg Asp Asn Tyr Pro Val His Phe Val Lys Ile Gly
            100                 105                 110

Lys Cys
```

Although preferred embodiments of the invention have been described above, the scope of the invention is limited only by the following claims:

I claim:

1. A purified protein that inhibits tumor cell growth and having the amino acid sequence shown in SEQ ID NO:1.

2. A purified protein that inhibits tumor cell growth and having the amino acid sequence shown in SEQ ID NO:2.

3. A purified protein that inhibits tumor cell growth and having the amino acid sequence shown in SEQ ID NO:3.

4. A purified protein that inhibits tumor cell growth and having the amino acid sequence shown in SEQ ID NO:4.

5. A purified variant of the protein having the amino acid sequence shown on SEQ ID NO:1, wherein the variant inhibits growth of human tumor cells, and wherein said variant differs from the protein of SEQ ID NO:1 solely by conservative substitution of one or more of the amino acid residues at positions 6, 9, 13, 27, 28, 32, 34, 35, 44, 51, 57, 63, 75, 80, 81, 83, 92, 95, and 111.

6. A purified variant of the protein having the amino acid sequence shown on SEQ ID NO:1, wherein the variant inhibits growth of human tumor cells, and wherein said variant differs from the protein of SEQ ID NO:1 in that the amino acid residue at position 6 may be Arg or Lys, the amino acid residue at position 9 may be Glu or Val, the amino acid residue at position 13 may be Thr or Val or Ala, the amino acid residue at position 27 may be Asn or Thr, the amino acid residue at position 28 may be Arg or Ser or Lys, the amino acid residue at position 32 may be Asp or Asn, the amino acid residue at position 34 may be Ala or Asp, the amino acid residue at position 35 may be Tyr or Phe, the amino acid residue at position 44 may be Ile or Val, the amino acid residue at position 51 may be Thr or Asn, the amino acid residue at position 57 may be Glu or Asp, the amino acid residue at position 63 may be Thr or Ser, the amino acid residue at position 75 may be Thr or Pro, the amino acid residue at position 80 may be Lys or Asn, the amino acid residue at position 81 may be Asn or Lys, the amino acid residue at position 83 may be Ile or Lys, the amino acid residue at position 92 may be Thr or Glu, the amino acid residue at position 95 may be Phe or Tyr, and the amino acid residue at position 111 may be Thr or Ile.

7. A purified protein that is a conservatively modified variant of the amino acid sequence shown in SEQ ID NO:1 and that inhibits tumor cell growth.

8. A purified protein that is a conservatively modified variant of the amino acid sequence shown in SEQ ID NO:2 and that inhibits tumor cell growth.

9. A purified protein that is a conservatively modified variant of the amino acid sequence shown in SEQ ID NO:3 and that inhibits tumor cell growth.

10. A purified protein that is a conservatively modified variant of the amino acid sequence shown in SEQ ID NO:4 and that inhibits tumor cell growth.

* * * * *